United States Patent [19]

Talley

[11] Patent Number: 5,348,543
[45] Date of Patent: Sep. 20, 1994

[54] HYPODERMIC NEEDLE GUARD SYSTEM

[76] Inventor: John Talley, 1550 Valencia, Newport Beach, Calif. 92660

[21] Appl. No.: 53,799

[22] Filed: Apr. 28, 1993

[51] Int. Cl.$^5$ ............................................. A61M 5/32
[52] U.S. Cl. ................................. 604/192; 604/263
[58] Field of Search ............... 604/110, 192, 187, 263; 206/365, 366, 369

[56] References Cited

U.S. PATENT DOCUMENTS

| | | | |
|---|---|---|---|
| 4,659,330 | 4/1987 | Nelson et al. | 604/192 |
| 4,737,149 | 4/1988 | Gillilan | 604/192 |
| 4,955,865 | 9/1990 | Steiner et al. | |
| 5,183,469 | 2/1993 | Capaccio | 604/192 |

FOREIGN PATENT DOCUMENTS 2209470  5/1989  United Kingdom ................ 604/192

*Primary Examiner*—John D. Yasko
*Attorney, Agent, or Firm*—Charles H. Thomas

[57] ABSTRACT

A system is provided for the prevention of accidental needle pricks from the needle of a hypodermic syringe and for supporting the syringe in an upright disposition. A hypodermic syringe, having a conventional needle cap, is provided with a cap holder that includes both a suction cup and a sleeve having an open mouth and projecting upwardly therefrom. The suction cup is secured to a smooth surface by suction and the needle cap is inserted into the open mouth of the tube holder of the invention. Thereafter, with a single hand the hypodermic syringe can be capped by pushing the needle thereof into the needle cap, which is held stationary and stable by means of the cap holder. Preferably, the cap holder is provided with a retainer which may take the form of an elastic band secured relative to the cap holder sleeve. Once the hypodermic syringe has been inserted into the needle cap that is frictionally engaged within the cap holder sleeve, the elastic band is stretched and elastically distended to engage the laterally projecting finger support ears of the hypodermic syringe. The entire assembly can thereupon be safely moved and discarded.

6 Claims, 2 Drawing Sheets

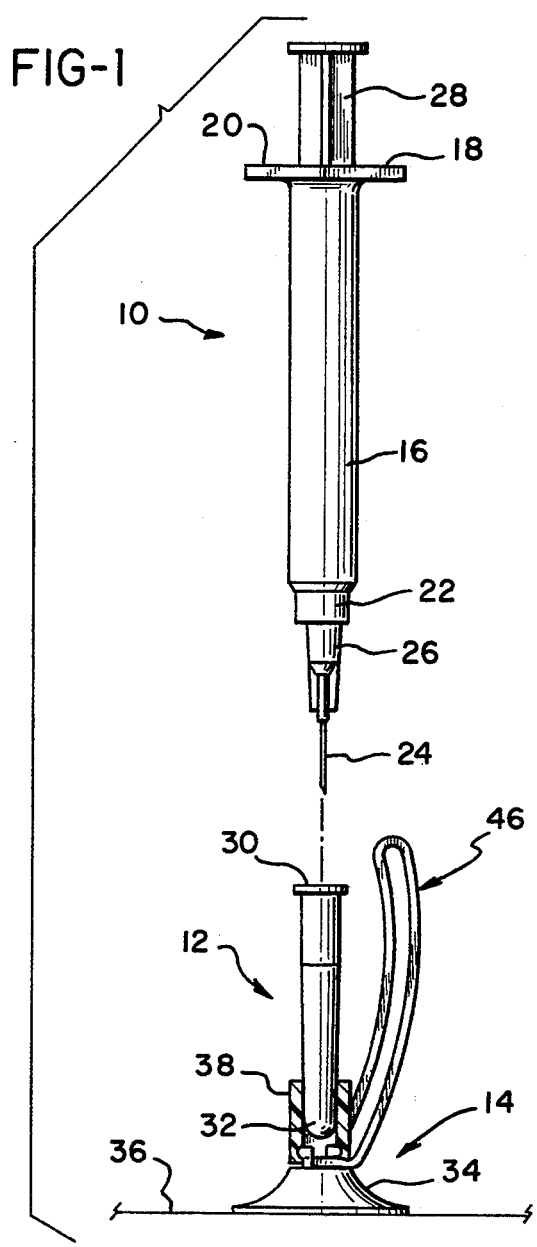
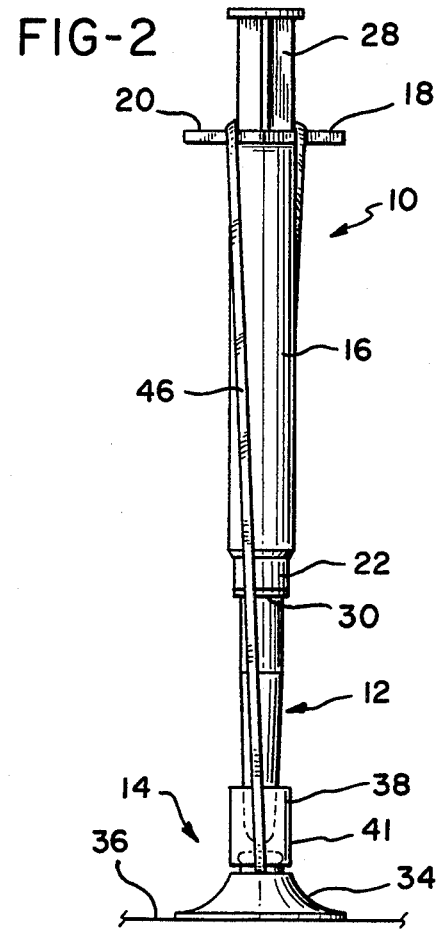
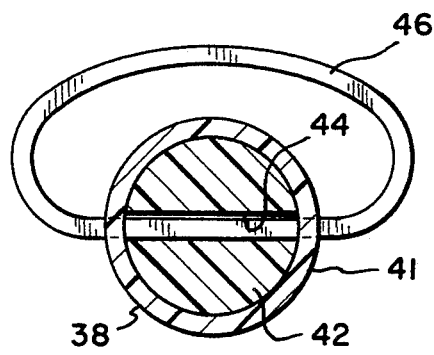
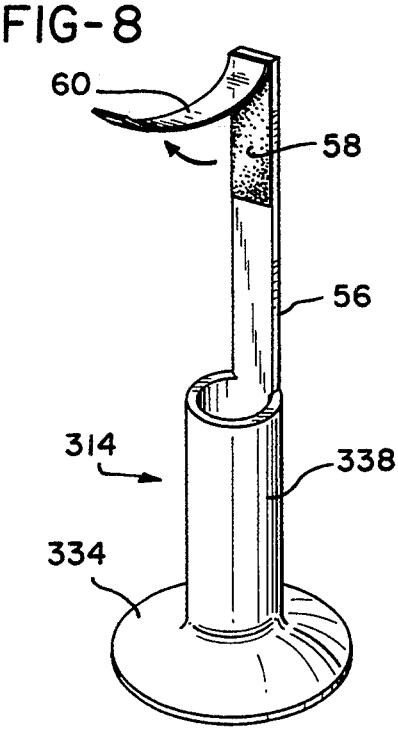

FIG-3
FIG-5
FIG-7
FIG-6
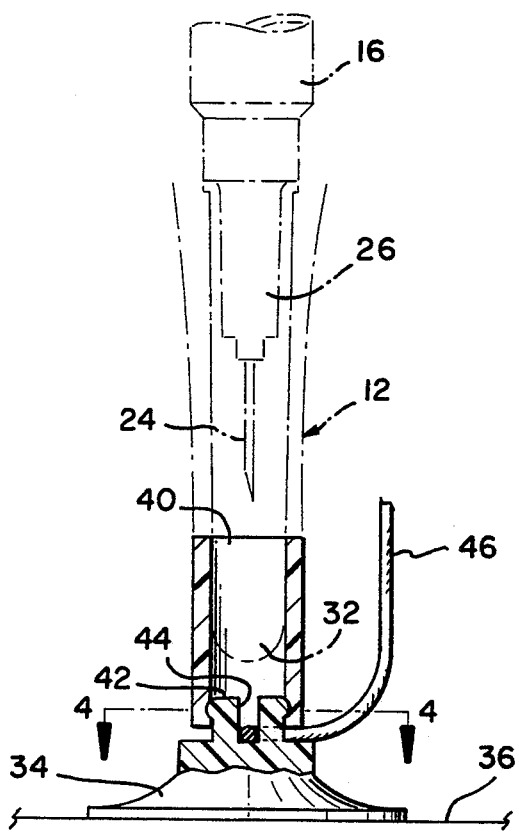
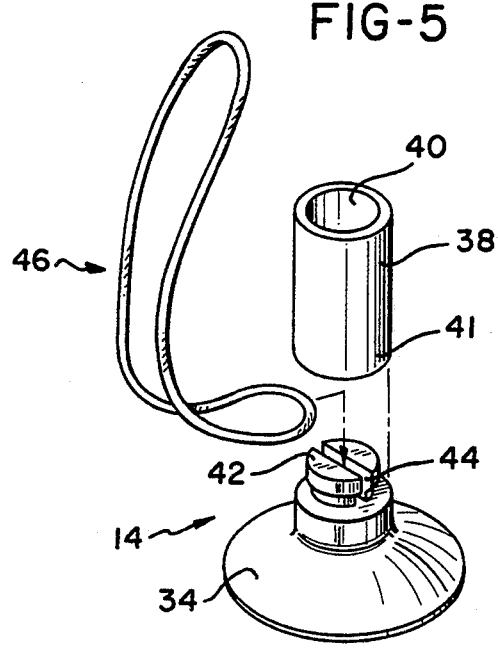
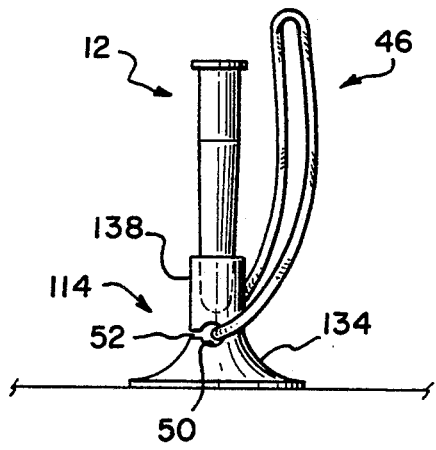
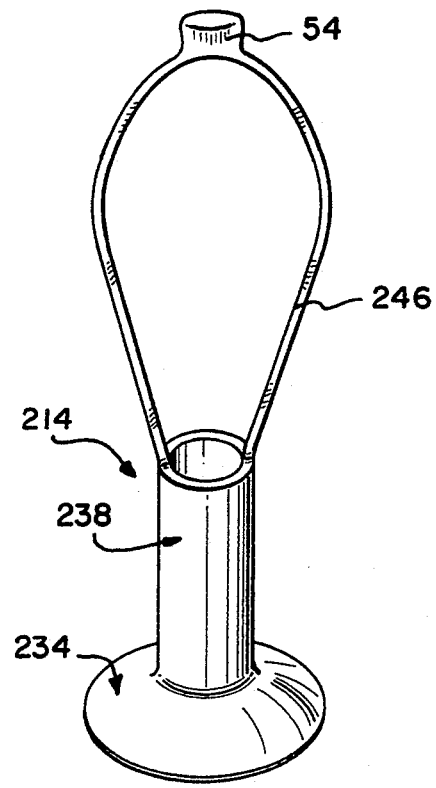

HYPODERMIC NEEDLE GUARD SYSTEM

BACKGROUND OF THE INVENTION

1. Field of the Invention

The present invention is related to a method and apparatus for preventing accidental pricks from needles of hypodermic syringes and for supporting hypodermic syringes.

2. Description of the Prior Art

Most hypodermic syringes now in use by medical personnel in hospitals and physician's offices are of a disposable type. Such syringes are typically manufactured entirely of plastic, except for the needle and in some cases the needle base. Such a hypodermic syringe includes a cylindrical barrel which narrows to a luer lock fitting at one end and has an opposite open end from which a pair of finger support flanges extend laterally outwardly in diametrical opposition to each other. A plastic plunger having a piston on its tip is inserted into the open end of the syringe barrel. A conventional hypodermic syringe also includes a metal needle element having an elongated, hollow needle with a somewhat larger cylindrical annular needle base with a radially outwardly directed lip at its open end. The lip of the needle base is coupled to the luer lock fitting of the barrel with a twisting or screwing action.

A conventional hypodermic syringe also includes a needle guard or cap in the form of a hollow, elongated plastic structure. The needle cap receives the syringe needle through an open, accessible end that fits snugly over the needle base in frictional engagement therewith. The opposite end of the needle cap is a closed or blind end.

To use a hypodermic syringe, the needle cap is removed and the distal tip of the needle is inserted into a liquid to be injected. The plunger is then retracted from the barrel, thus drawing liquid into the barrel, through the needle by means of suction. Filling of the syringe can either be performed locally in a hospital or in a physician's office. Often, however, the syringe barrel arrives at the medical facility pre-loaded with a liquid therein.

In either event, when the liquid is to be injected into a patient the distal tip of the needle is pressed into the skin of the patient and the plunger is depressed using the thumb of one hand with two fingers of the same hand bearing against the undersides of the laterally projecting finger support flanges. Once the liquid has been injected, the needle is withdrawn from the skin of the patient. If the entire contents of the syringe have been injected into the patient, the syringe must be discarded. Alternatively, in some cases several applications of a liquid in the syringe must be applied to different areas of the skin of the patient during the course of a surgery. In either event, the sharp needle, once having penetrated and then been withdrawn from the skin of the patent, represents a considerable hazard. Therefore, the needle is normally capped or sheathed.

The cap for a needle of a conventional medical syringe is an elongated, hollow sheath, closed at one end and having an open mouth at the opposite end. To replace the cap on the needle the physician or nurse must grasp the cap in one hand and the hypodermic syringe in the other and move the needle into the open mouth of the cap until the mouth is secured by friction about the base of the needle. However, the physician or nurse will occasionally misjudge the alignment between the needle and the cap and accidentally stick the fingers or thumb of the hand grasping the barrel-shaped cap with the needle. This can occur when the needle either passes longitudinally alongside the cap to prick the finger of the physician or nurse, or by an even smaller misalignment in which the needle enters the interior wall of the cap at an angle and is deflected laterally outwardly therethrough. In the latter instance the needle can pass outwardly entirely through the wall structure of the cap and prick the hand of the physician or nurse holding the cap.

Not only are needle pricks painful and distracting to the physician or nurse performing the surgery, but they can be extremely dangerous. A physician or nurse can contract hepatitis due to an accidental needle prick in capping a hypodermic syringe which has been withdrawn from the skin of a patient already infected with hepatitis. Likewise, other viral diseases can similarly be transmitted accidentally. The concern with respect to accidental needle pricks in the medical profession is now particularly acute due to the spreading prevalence of the deadly AIDS virus.

Several different approaches have been employed to attempt to eliminate the danger of accidental needle pricks following use of a hypodermic syringe. One approach is to construct the hypodermic syringe with a sleeve reciprocally mounted relative to the barrel of the syringe. After using the syringe the sleeve is pulled longitudinally along the barrel and over the needle until it provides a cylindrical annular guard disposed about the needle. Some typical reciprocal sliding needle sheaths or sleeves are disclosed in U.S. Pat. Nos. 4,747,837; 4,840,619; 4,968,304; and 4,723,943. However, the provision of a sliding sheath and the interlocking mechanisms associated therewith adds considerably to the complexity and expense of fabrication of the disposable hypodermic syringe product. Also, such systems require the physician or nurse utilizing the syringe to employ both hands in order to slide the sheath over the needle.

Another approach which has been employed to reduce the likelihood of needle pricks is to employ a large device that grips the needle cap while protecting the hand of the user. One such device is depicted in U.S. Pat. No. 4,955,865. This device is a hand held needle cad holder of rather intricate and expensive construction. This needle unsheathing and re-sheathing and handling apparatus is quite expensive, compared to the cost of disposable hypodermic syringes, and requires two hands for operation. A variation of this system is sold as a recapper stand by On-Guard Systems, Inc. located in Denver, Colo. This stand is provided with a base that rests upon a flat horizontal surface and has essentially the same operating mechanism as that described in U.S. Pat. No. 4,955,865. However, although this stand allows a needle to be recapped using one hand, it is quite expensive when considered in relation to the minimal expense of a conventional hypodermic syringe.

SUMMARY OF THE INVENTION

The present invention provides a simple, economical, but extremely effective system for recapping the needle of a hypodermic syringe without exposing the user to the risk of needle pricks. Also, the system of the present invention allows the user to recap a needle using only one hand. In addition the invention provides a convenient stand or pedestal which can hold a needle in an upright disposition.

In one broad aspect the present invention may be considered to be a cap holder for a hypodermic syringe comprising a tubular sleeve having an open, accessible end with an internal cross section that snugly receives a cap for the needle of a hypodermic syringe therewithin, and an opposite end, and a suction cup located at the opposite end of the sleeve and directed away from the open end thereof.

Utilizing the cap holder of the invention, the suction cup can be pressed against any smooth surface, such as a desk, counter, medicine tray, and even curved surfaces, such as bed frames. The suction cup will adhere to all such smooth surfaces and holds the sleeve projecting outwardly from the surface to which the suction cup is attached. The user then inserts the needle cap into the open end of the sleeve of the cap holder, and releases the cap holder. The cap holder is held in an upright disposition by the sleeve, which in turn is held in a stationary location by means of the suction cup. Using only one hand, the hypodermic syringe can then be directed toward the cap and the needle is inserted into the cap until the cap frictionally engages the base of the needle in a conventional manner. The needle is thereupon safely capped and the entire syringe, cap and needle can be discarded or stored for further use, as appropriate. The suction cup can be released from the surface to which it is attached by breaking the suction in a conventional manner.

The hypodermic syringe cap holder of the invention also serves the purpose of providing a convenient, clean device for holding a hypodermic syringe. In conventional practice medical personnel typically carry a capped hypodermic syringe on a tray. When an injection is to be given the cap is withdrawn from the needle. Sometimes, however, the physician or nurse administering the injection discovers that some preliminary step must be taken before actually administering the injection and after the needle cap has been withdrawn. For example, a patient must sometimes be repositioned, or some obstacle must be moved out of the way. In conventional practice the only alternative is to recap the needle, with the attendant danger of a needle prick, or lay the needle back on the tray, where it is subject to contamination.

By employing the cap holder of the invention the person administering the injection is provided with a convenient arrangement for holding the needle in an upright disposition and without danger of contamination. That is, if the hypodermic syringe is prematurely withdrawn from the needle cap, the needle cap is merely pressed into the open end of the cap holder, the suction cup of the cap holder is pressed against the tray or some other smooth surface, and, using only one hand, the needle of the syringe is inserted, back into the needle cap until seated. The cap holder thereby supports the hypodermic syringe, ready for use, in an upright disposition and a clean and sterile manner, and without the possibility of inadvertent needle pricks.

Preferably, the cap holder of the invention is provided with a syringe retainer releasably attachable to the hypodermic syringe. This retainer may take the form of an elastic loop or band secured to the cap holder at the transition between the suction cup and the sleeve. The loop may be formed of an ordinary rubber band, or by a plastic loop which is sufficiently resilient to pass over and capture at least one of the laterally projecting finger support flanges at the remote extremity of the barrel. By employing such an elastic loop the hypodermic syringe may be effectively lashed down so that the needle remains covered by the needle cap and the needle cap remains in position in the sleeve of the cap holder.

The cap holder of the invention is extremely economical to manufacture and may be disposed of along with the disposable hypodermic syringe without inordinately increasing the cost of the product. The cap holder may be fabricated of any conventional plastic material that has some resiliency. Alternatively, it can be manufactured of rubber.

In another broad aspect the invention may be considered to be a combination of a hypodermic syringe having a barrel with a needle projecting therefrom, a cap for the needle having an open end securable relative to the barrel to receive the needle therewithin and an opposite blind end, and a cap holder formed with a sleeve having an open mouth at one end to receive the blind end of the cap in frictional engagement therewith and having a suction cup at an opposite end. The suction cup is engageable by suction with a flat surface to support the cap holder to receive the cap with the needle of the hypodermic syringe therewithin.

In still another broad aspect the invention may be considered to be a method of capping a hypodermic syringe formed with a barrel having a needle projecting therefrom and a cap for the needle formed with an open end and an opposite closed end. The method of the invention is comprised of the steps of: securing to a smooth supporting surface a cap holder having a sleeve formed with an open mouth at one end and a suction cup at its opposite end by pressing the suction cup against the smooth supporting surface, inserting the closed end of the cap into the mouth of the cap holder, and inserting the needle of the hypodermic syringe into the open end of the cap holder. As previously noted, the sleeve preferably has a retainer secured thereto. In that case the method includes the further step of releasably securing the retainer to the hypodermic syringe.

The invention may be described with greater clarity and particularity by reference to the accompanying drawings.

DESCRIPTION OF THE DRAWINGS

FIG. 1 is a side elevational view, partially in section, illustrating one embodiment of the invention and manner of the practice of the method thereof.

FIG. 2 is a side elevational view of the embodiment of FIG. 1 illustrating a hypodermic syringe secured within the cap holder of the invention.

FIG. 3 is an elevational detail of the cap holder of the invention showing the embodiment of FIG. 1 partially in section.

FIG. 4 is a sectional plan detail taken along the lines 4—4 of FIG. 3.

FIG. 5 is an exploded perspective view of the cap holder of FIGS. 1-4.

FIG. 6 is a perspective view showing an alternative embodiment of the cap holder of the invention.

FIG. 7 is a side elevational view showing another alternative embodiment of the cap holder of the invention with a hypodermic syringe cap inserted therein.

FIG. 8 is a perspective view of still another alternative embodiment of the cap holder of the invention.

DESCRIPTION OF THE EMBODIMENTS AND IMPLEMENTATION OF THE METHOD

FIGS. 1 through 5 illustrate one preferred embodiment of a combination according to the invention including a hypodermic syringe indicated generally at 10, a cap 12 for the hypodermic syringe 10, and a cap holder 14 according to the invention.

The hypodermic syringe 10 is a conventional plastic, disposable syringe having a cylindrical annular barrel 16. The top of the syringe barrel 16 is open and a pair of laterally projecting finger support flanges 18 and 20 extend radially outwardly therefrom. At its opposite end the barrel narrows to a collar 22 which is internally threaded to form a luer lock fitting. A needle structure including an elongated, narrow hollow metal needle 24 and a plastic needle base 26 is secured to the barrel collar 22 by a luer lock fitting in a conventional manner. The hypodermic syringe 10 also has a plunger 28 which works reciprocally within the barrel 16 to expel a liquid to be injected from the tip of the needle 24.

The needle cap 12 is also a conventional structure and is formed as an elongated, annular housing or casing of a generally frustoconical configuration. The upper end of the cap 12 is open and has a short, radial lip 30 projecting outwardly therefrom. The opposite blind end 32 of the needle cap 12 is rounded and closed.

The cap holder 14 is illustrated in greatest detail in FIG. 3. The cap holder 14 is fabricated of a soft, resilient plastic and comprises a generally conical suction cup 34 disposed concave downwardly toward a smooth surface 36. The suction cup 34 is releasably secured to the surface 36 in a conventional manner by the application of downward pressure which forces air out from beneath the peripheral edge of the suction cup 34, thus flattening the suction cup 34 as illustrated in FIGS. 1–3. Due to the resiliency of the cap holder 14, the suction cup 34 tends to return to its un-deformed condition, thereby creating a suctional force against the surface 36.

The cap holder 14 is also formed with a cylindrical, annular resilient plastic sleeve 38. The plastic sleeve 38 has an internal diameter of approximately three eighths of an inch, so as to snugly receive the lowermost end 32 of those needle caps 12 that are most widely employed for use with medical hypodermic syringes 10. At its upper extremity the sleeve 38 has an open mouth 40 that receives the blind end 32 of the needle cap 12 in frictional engagement therewithin. The upper end of the suction cup 34 terminates in a short, upwardly projecting stud or stump 42 having a downwardly directed, transversely extending narrow slot 44 defined therewithin. The slot 44 extends across the diameter of the stud 42 and is deep enough to receive and laterally constrain a rubber band 46 therewithin. The rubber band 46 is a conventional rubber band formed as an endless loop and capable of resiliently stretching a considerable distance.

As illustrated in FIGS. 1–5, one section of the rubber band 46 is inserted downwardly into the slot 44 defined in the upwardly projecting stud 42. The sleeve 38 is then pressed downwardly so that the interior wall of its lower extremity is secured by frictional engagement about the outer surface of the upwardly projecting stud 42. Both the sleeve 38 and the stud 42 are formed of resilient, plastic structures and are configured so that the sleeve 38 fits snugly over the top of the stud 42. The lower end of the sleeve 38 is thereupon engaged by the force of friction with the outer surface of the stud 42, while the rubber band 46 lies within the groove 44 and passes beneath the sleeve 38 on opposite sides thereof. The lower end 41 of the sleeve 38 is pressed downwardly against the rubber band 46 to thereby immobilize it and secure the rubber band 46 relative to the sleeve 38.

The operation of the invention may best be described with reference to FIGS. 1–3. As illustrated in FIG. 3, the suction cup 34 of the cap holder 14 is first pressed downwardly against the smooth surface 36 so that the suction cup 34 adheres thereto by means of suction. The blind end 32 of the needle cap 12 is then pushed downwardly into the open mouth 40 of the sleeve 38 of the cap holder 14. The sleeve 38 is sufficiently resilient to distend slightly radially outwardly, so that its inner surface at the mouth 40 frictionally engages the lower extremity of the needle cap 12. The cap 12 and cap holder 14 are thereupon ready to receive the hypodermic syringe 10.

After the hypodermic syringe 10 has been used to give a patient an injection, the syringe 10 is directed downwardly with the needle 24 axially aligned with the upper, open end of the needle cap 12. The syringe 10 is then moved downwardly toward the cap 12 and cap holder 14 so that the needle 24 enters into the central opening in the upper end of the needle cap 12.

It should be noted that the step of insertion of the hypodermic syringe 10 is normally performed with a single hand. Should the needle 24 be misaligned relative to the needle cap 12, it is possible that the needle 24 will penetrate the upright annular wall of the needle cap 12. However, even if this occurs the user is not exposed to any danger of a needle prick. To the contrary, the users hands are not required to hold the needle cap 12 upright, since the suction cup 34 of the cap holder 14 performs this function.

Once the hypodermic syringe 10 has been fully inserted into the cap 12, the interior surface of the upper walls of the cap 12 distends slightly and frictionally engages the base 26 of the needle structure. Since the interior walls of the upper extremity of the sleeve 38 likewise fractionally grip the outer surface of the blind end 32 of the needle cap 12, the suction of the suction cup 34 can be broken in a conventional manner, and the entire hypodermic assembly lifted from the surface 36 and discarded, or even stored for further use or analysis, as appropriate.

Preferably, the elastic loop 46 is employed so as to firmly hold the needle cap 12 in position to cover the needle 24. Once the needle of the hypodermic syringe 10 has been inserted into the cap 12, as depicted in phantom in FIG. 3, the user elastically stretches the rubber band 46 and pulls the portion thereof located remote from the stud 42 upwardly and over the top of the plunger 28. The user then releases the rubber band, which due to its resiliency, retracts downwardly, but is restrained from full retraction by the laterally projecting finger supports 18 and 20, as depicted in FIG. 2. Thus, the elastic band 46 forms a further safeguard that holds the needle cap 12 in position covering the needle 24.

It may well be desireable for the cap holder 14 to be manufactured in a distinctive color, such as red. This provides a warning to anyone who encounters the combined assembly of the hypodermic syringe 10, the cap 12, and the cap holder 14 that the syringe 10 has been used and may be contaminated.

Numerous different modifications of the system of the invention are possible. For example, while the cap holder 14 of the embodiment of FIGS. 1–4 is formed of component parts, namely a tubular annular structure which fits onto an upwardly projecting stud of the suction cup 34, the sleeve and suction cup can be formed as a unitary structure. One embodiment of such a unitary cap holder 114 is illustrated in FIG. 7. In that embodiment the resilient sleeve 138 and the suction cup 134 are formed together as a single molded unit, with the sleeve 138 constituting a hollow, upwardly projecting structure atop the suction cup 134. The needle cap 12 fits into the open, upwardly facing mouth of the sleeve 138 in the same manner and by means of the same frictional engagement as with the embodiment of FIGS. 1–5.

Since the sleeve 138 and suction cup 134 of the cap holder 114 of FIG. 7 are formed as a unitary embodiment, a different arrangement must be employed if a rubber band 46 is to be utilized therewith as a restraining device. To this end a transverse opening 50 is defined through the molded structure forming the suction cup 134 and sleeve 138 at the transition therebetween, and a narrow, transverse slot 52 is defined in that structure at the same location. The slot 52 extends perpendicularly outwardly relative to the alignment of the opening 50. The rubber band 46 can then be pressed into the transverse slot 52 so that it resides within the opening 50 and is thereby coupled to the sleeve 138 and suction cup 134. The rubber band 46 can thereupon be employed to restrain the hypodermic syringe 10 in the same manner as depicted in FIG. 2.

FIG. 6 illustrates still another embodiment of the invention. In the embodiment of FIG. 6 the cap holder 214 is formed as a completely unitary structure that includes not only the suction cup 234 and sleeve 238, but also an elastic loop 246 projecting upwardly from the upper end of the sleeve 238 at diametrically opposite sides of the open, accessible end of the sleeve 238. The plastic loop 246 is thin enough so that it can be stretched to the extent necessary to engage at least one of the laterally projecting finger support flanges 18 and 20 of the hypodermic syringe 10. Elastic deformation of the loop 246 is performed by pulling on an enlarged, flat pull-tab 54 located at the center of the loop 246. The steps of the method of the invention employing the cap holder 214 are performed in precisely the same manner as described in conjunction with the embodiments of FIGS. 1–5. As in the other embodiment, the retainer formed by the elastic loop is releasably attachable to the hypodermic syringe 10 to hold the hypodermic syringe 10 snugly seated in the needle cap 12 and the needle cap 12 snugly seated in the cap holder.

FIG. 8 of the drawings illustrates still another embodiment of the invention. Like the cap holder 214, the cap holder 314 is formed as a unitary structure and has a suction cup 334 at its base and a cylindrical, annular sleeve 338 projecting upwardly therefrom. However, at the top of the open end of the sleeve 338 a narrow portion of the wall thereof projects upwardly as an elongated strip 56. The strip 56 extends upwardly a sufficient distance so that it reaches beyond the length of the cap 12 to the level of the barrel 16 of the hypodermic syringe 10.

At its upper extremity the strip 56 has an area 58 of pressure sensitive adhesive thereon. When distributed for use the cap holder 314 has a strip of release paper 60 covering the area of the pressure sensitive adhesive 58.

However, when the hypodermic syringe 10 is to be restrained within the cap holder 314, the strip of release paper 60 is removed and discarded. The pressure sensitive adhesive 58 is then pressed against the wall of the barrel 16 and adheres thereto. The hypodermic syringe 10 is thereupon restrained from removal from the cap 24, not only by the frictional force of engagement therewith, but also by virtue of the restraint provided by the retaining strip 56.

Undoubtedly, numerous variations and modifications of the invention will become readily apparent to those familiar with the fabrication and use of hypodermic syringes. For example, if the suction cup and the sleeve are formed as a unitary structure, the sleeve might not be stiff enough to hold the needle cap holder 12 stable. However the sleeve of the cap holder of the invention may be equipped with a tubular internal, stiffening liner of a more rigid plastic or metal to steady the sleeve of the needle holder. Accordingly, the scope of the invention should not be construed as limited to this specific embodiments and manner of implementation depicted and described herein.

I claim:

1. A holder for a hypodermic syringe comprising: a resilient tubular sleeve having an open accessible end with an internal cross section that receives the needle of a hypodermic syringe therewithin and an opposite end and a hollow interior extending between said ends, a resilient suction cup located at said opposite end of said sleeve and directed away from said open end thereof, so as to be engageable by suction with a flat surface to support said tube in an upright disposition directed outwardly away from said flat surface, and wherein said suction cup includes structure that extends transversely across said opposite end of said tubular sleeve so as to close said opposite end and isolate said hollow interior of said sleeve from said flat surface beneath said suction cup, thereby preventing the flow of air therebetween, and an elastic loop secured relative to said sleeve and elastically stretchable for releasable engagement with a hypodermic syringe inserted into said sleeve.

2. A holder according to claim 1 further comprising an elastic loop secured relative to said sleeve and elastically stretchable for releasable engagement with a hypodermic syringe inserted into a cap therefor that is disposed within said sleeve.

3. A holder according to claim 1 wherein said suction cup and said sleeve are both formed as a single, unitary structure, and wherein said elastic loop is formed in the same aforesaid single, unitary structure emanates from opposite sides of said sleeve to said open accessible end thereof.

4. A holder according to claim 3 wherein said elastic loop has an enlarged pull-tab at its center.

5. In combination, a hypodermic syringe having a barrel with a needle projecting therefrom, a cap for said needle having an open end securable relative to said barrel to receive said needle therewithin and an opposite blind end, and a cap holder formed with a resilient sleeve having a hollow interior with an open mouth at one end to receive said blind end of said cap in frictional engagement therewithin and having a resilient suction cup at an opposite end, whereby said suction cup is engageable by suction with a flat surface to support said cap holder in an upright disposition directly outwardly away from said flat surface to receive said cap with said needle of said hypodermic syringe therewithin, and wherein said suction cup includes structure that extends transversely across said opposite end of said tubular sleeve so as to close said opposite end and isolate said hollow interior of said sleeve from said flat surface beneath said suction cup, thereby preventing the flow of air therebetween, and wherein said cap holder is further comprised of a syringe retainer in the form of an elastic loop releasably attachable to said hypodermic syringe and secured relative to said sleeve.

6. A method of capping a hypodermic syringe formed with a barrel having a needle projecting therefrom and a cap for said needle formed with an open end and an opposite closed end, and wherein and said barrel has a pair of laterally projecting finger support flanges extending therefrom remote from said needle, the steps comprising:

securing to a smooth supporting surface a cap holder having a resilient sleeve formed with a hollow interior, an open mouth at one end and a suction cup at its opposite end so as to be engageable by suction with a flat surface to support said tube in an upright disposition directed outwardly away from said flat surface, by pressing said suction cup against said smooth supporting surface, and isolating said hollow interior of said sleeve from said flat surface beneath said suction cup to prevent the flow of air therebetween, and wherein said sleeve has a retainer secured relative thereto in the form of an elastic loop, inserting said closed end of said cap into said mouth of said cap holder, inserting said needle of said hypodermic syringe into said open end of said cap holder, and releasably securing said retainer to said hypodermic syringe by elastically stretching said elastic loop and releasably engaging said elastic loop about said finger support flanges.

* * * * *